United States Patent
Kamiya et al.

(10) Patent No.: US 9,433,605 B2
(45) Date of Patent: Sep. 6, 2016

(54) METHOD FOR PROMOTING SYNTHESIS OF TISSUE COLLAGEN

(71) Applicant: Kyowa Hakko Bio Co., Ltd., Chiyoda-ku, Tokyo (JP)

(72) Inventors: Toshikazu Kamiya, Tsuchiura (JP); Ayako Kamimura, Tsukuba (JP); Yoko Kawada, Tsukuba (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 13/856,566

(22) Filed: Apr. 4, 2013

(65) Prior Publication Data
US 2013/0225650 A1    Aug. 29, 2013

Related U.S. Application Data

(62) Division of application No. 12/280,846, filed as application No. PCT/JP2007/055977 on Mar. 23, 2007, now abandoned.

(30) Foreign Application Priority Data

Mar. 23, 2006   (JP) ................. 2006-079921

(51) Int. Cl.
| | |
|---|---|
| A01N 25/34 | (2006.01) |
| A61K 31/40 | (2006.01) |
| A61K 31/401 | (2006.01) |
| A23G 3/36 | (2006.01) |
| A23G 3/44 | (2006.01) |
| A23K 1/16 | (2006.01) |
| A23L 1/305 | (2006.01) |
| C07D 207/16 | (2006.01) |

(52) U.S. Cl.
CPC .............. *A61K 31/401* (2013.01); *A23G 3/36* (2013.01); *A23G 3/44* (2013.01); *A23K 1/1634* (2013.01); *A23L 1/3051* (2013.01); *C07D 207/16* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,932,638 A | 1/1976 | Coirre et al. |
| 5,827,874 A | 10/1998 | Meyer et al. |
| 6,692,754 B1 | 2/2004 | Makimoto et al. |
| 2004/0082502 A1 | 4/2004 | Gans |
| 2006/0034781 A1 | 2/2006 | Takahashi et al. |
| 2007/0065396 A1* | 3/2007 | Morariu ........................ 424/74 |
| 2007/0259808 A1* | 11/2007 | Gans ............................. 514/2 |
| 2007/0293559 A1 | 12/2007 | Kagami et al. |

FOREIGN PATENT DOCUMENTS

| | | |
|---|---|---|
| EP | 1 547 594 | 6/2005 |
| JP | 1995-278012 | 10/1995 |
| JP | 2000-201649 | 7/2000 |
| JP | 2001-1131084 | 5/2001 |
| JP | 2003-137807 | 5/2003 |
| JP | 2004-035527 | 2/2004 |
| JP | 2004-315384 | 11/2004 |
| JP | 2005-289928 | 10/2005 |
| JP | 2006-345824 | 12/2006 |
| WO | 1999/24046 | 5/1999 |
| WO | 2000-051561 | 9/2000 |
| WO | 2004/039368 | 5/2004 |

OTHER PUBLICATIONS

Natural Baby Skin Care Tips, Retrieved on [Aug. 26, 2014], Retrieved from URL:<http://www.webmd.com/parenting/baby/baby-skin-10/skin-care-tips>.*
Kelman, et al., "Effect of N-Acetyl-cis-4-Hydroxyproline on Collagen Synthesis", Experimental and Molecular Pathology, vol. 28 (1978) 58-64.
Adams, et al., Hydroxyproline Metabolism, J. Biol., Chem., vol. 235, No. 12 (1960) 3492-98.
Valle et al., Genetic Evidence for a Common Enzyme Catalyzing the Second Step in the Degradation of Proline and Hydroxyproline, J. Clin. Invest., vol. 64 (1979) 1365-70.

* cited by examiner

*Primary Examiner* — Nannette Holloman
(74) *Attorney, Agent, or Firm* — Fitzpatrick, Cella, Harper & Scinto

(57) ABSTRACT

An object of the present invention is to provide an oral preparation for promoting synthesis of tissue collagen, an oral preparation for promoting healing of skin wounds or an oral preparation for preventing or improving skin wrinkles or sagging, which is safe and has an excellent effect. The present invention can provide an oral preparation for promoting synthesis of tissue collagen, an oral preparation for promoting healing of skin wounds or an oral preparation for preventing or improving skin wrinkles or sagging, which comprises hydroxyproline or a salt thereof as an active ingredient.

12 Claims, 1 Drawing Sheet

METHOD FOR PROMOTING SYNTHESIS OF TISSUE COLLAGEN

This application is a divisional of application Ser. No. 12/280,846 filed Aug. 27, 2008, which in turn is a 371 of PCT Application No. PCT/JP2007/055977 filed Mar. 23, 2007 which claims priority of Japanese Application No. 079921/06 filed Mar. 23, 2006.

TECHNICAL FIELD

The present invention relates to an oral preparation for promoting synthesis of tissue collagen, an oral preparation for promoting healing of skin wounds and an oral preparation for preventing or improving skin wrinkles or sagging, which comprise hydroxyproline or a salt thereof as an active ingredient.

BACKGROUND ART

Collagen is a protein which is the main component of extracellular matrix filling the spaces between cells or groups of cells in living tissues and is said to sometimes comprise nearly 30% of the total protein in the body of mammals (see non-patent document No. 1).

Collagen forms a fibrous structure or a membrane structure and its primary function is to maintain, support, bind and reinforce the tissue structure. Collagen exists in abundance in skin, bones, tendons, ligaments, cornea, blood vessels, etc. Decrease and denaturation of tissue collagen is considered to be a major factor for wrinkles, sagging skin, osteoporosis and the like which are induced by aging of these tissues. Actually, there are reports that tissue collagen remarkably decreases by long time exposure to sunlight (see non-patent document No. 2) and that lowering of metabolism of living components accompanying aging is triggered by the lowering of metabolism of collagen (see non-patent document No. 3).

Substances known to promote the synthesis of collagen include TGF β-1, which is a growth factor (see non-patent document No. 4), a plant extract (see patent-document No. 1), hydrolyzed collagen (see patent document Nos. 2 to 5) and an amino acid composition (see patent document No. 6). More specifically, the tripeptide Gly-Pro-Hyp is known as a sequence characteristic of hydrolyzed collagen showing the activity to promote the synthesis of collagen when orally ingested. However, it is also known that an amino acid composition whose constitutive ratio of constituent amino acids such as Gly, Pro and Hyp was made equal to that of collagen does not show the activity to promote the synthesis of collagen (see patent document No. 4).

On the other hand, an N-acyl derivative of hydroxyproline is known to have the activity to promote the synthesis of collagen when orally ingested (see non-patent document No. 4), and an external medicine containing an N-acetyl derivative of hydroxyproline is used as a wound-healing agent in Europe. It is also known that hydroxyproline and an N-acyl derivative of hydroxyproline have collagen synthesis promoting effect on cultured human fibroblasts, and when externally applied, they have the activity to prevent or decrease the formation of wrinkles (patent document No. 7). However, unknown are the activity to promote the synthesis of collagen, the activity to promote the healing of skin wounds and the activity to prevent or improve skin wrinkles or sagging of orally ingested hydroxyproline.

Patent document No. 1:
Japanese Published Unexamined Patent Application No. 35527/04
Patent document No. 2:
Japanese Published Unexamined Patent Application No. 278012/95
Patent document No. 3:
Japanese Published Unexamined Patent Application No. 201649/00
Patent document No. 4:
Japanese Published Unexamined Patent Application No. 131084/01
Patent document No. 5:
Japanese Published Unexamined Patent Application No. 137807/03
Patent document No. 6:
Japanese Published Unexamined Patent Application No. 289928/05
Patent document No. 7:
WO2000/051561 pamphlet
Non-patent document No. 1:
Seikagaku Jiten (Biochemical Dictionary), First Edition, Tokyo Kagaku Dojin, p. 480 (1984)
Non-patent document No. 2:
Karei to Hifu (Aging and Skin), Seishi Shoin, p. 35 (1986)
Non-patent document No. 3:
Mechanism and Control of Aging, IPC, p. 151 (1993)
Non-patent document No. 4:
Experimental & Molecular Pathology, Vol. 28, No. 1, p. 58-64 (1978)

DISCLOSURE OF THE INVENTION

Problems to be Solved by the Invention

An object of the present invention is to provide an oral preparation for promoting synthesis of tissue collagen, an oral preparation for promoting healing of skin wounds or an oral preparation for preventing or improving skin wrinkles or sagging, which is safe and has an excellent effect.

Means for Solving the Problems

The present invention relates to the following (1) to (10).
(1) An oral preparation for promoting synthesis of tissue collagen, which comprises hydroxyproline or a salt thereof as an active ingredient.
(2) The oral preparation for promoting synthesis of collagen tissue according to the above (1), wherein the tissue is skin.
(3) A method for promoting synthesis of tissue collagen, which comprises orally administering an effective amount of hydroxyproline or a salt thereof.
(4) Use of hydroxyproline or a salt thereof for the manufacture of an oral preparation for promoting synthesis of tissue collagen.
(5) An oral preparation for promoting healing of skin wounds, which comprises hydroxyproline or a salt thereof as an active ingredient.
(6) A method for promoting healing of skin wounds, which comprises orally administering an effective amount of hydroxyproline or a salt thereof.
(7) Use of hydroxyproline or a salt thereof for the manufacture of an oral preparation for promoting healing of skin wounds.
(8) An oral preparation for preventing or improving skin wrinkles or sagging, which comprises hydroxyproline or a salt thereof as an active ingredient.

(9) A method for preventing or improving skin wrinkles or sagging, which comprises orally administering an effective amount of hydroxyproline or a salt thereof.

(10) Use of hydroxyproline or a salt thereof for the manufacture of an oral preparation for preventing or improving skin wrinkles or sagging.

Effect of the Invention

The present invention provides an oral preparation for promoting synthesis of tissue collagen, an oral preparation for promoting healing of skin wounds or an oral preparation for preventing or improving skin wrinkles or sagging, comprising hydroxyproline or a salt thereof as an active ingredient, which is safe and has an excellent effect.

BEST MODES FOR CARRYING OUT THE INVENTION

Figure 1:
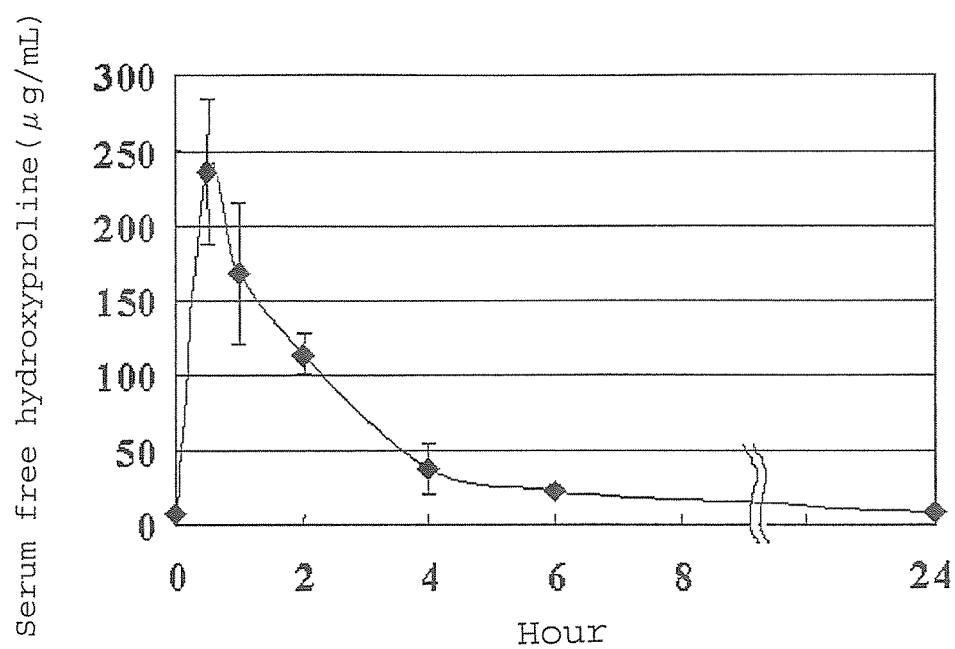
FIG. 1 is a graph showing the concentration of free hydroxyproline in serum after oral intake of hydroxyproline.

Hydroxyproline used in the present invention may be any of the stereoisomers of hydroxyproline. That is, hydroxyproline can exist as eight kinds of stereoisomers according to whether proline is in the D or L form, whether the hydroxyl group is located at the 3- or 4-position, and whether the stereoisomer is in the cis or trans form, and any of these stereoisomers can be employed in the present invention.

Specifically, hydroxyproline includes cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

Hydroxyproline is a kind of amino acid which exists widely in nature as the major amino acid component of collagen and as a constituent amino acid of elastin, and can be produced, for example, by acid hydrolysis of collagen derived from animals such as pig and cow, followed by purification by ordinary means.

Trans-4-hydroxy-L-proline can be produced by using proline 4-hydroxylase isolated from a microorganism belonging to the genus *Amycolatopsis* or *Dactylosporangium* (Japanese Published Unexamined Patent Application No. 313179/95). Cis-3-hydroxy-L-proline can be produced by using proline 3-hydroxylase isolated from a microorganism belonging to the genus *Streptomyces* (Japanese Published Unexamined Patent Application No. 322885/95) [Bioindustry, Vol. 14, No. 31 (1997)].

The above hydroxyprolines produced by using enzymes derived from microorganisms are superior in quality and are preferred as hydroxyproline used in the present invention.

The salts of hydroxyproline include acid addition salts, metal salts, ammonium salts, organic amine addition salts and amino acid addition salts.

Examples of the acid addition salts include inorganic acid addition salts such as hydrochloride, sulfate, nitrate and phosphate, and organic acid addition salts such as acetate, maleate, fumarate, citrate, malate, lactate, α-ketoglutarate, gluconate and caprylate.

Examples of the metal salts are alkali metal salts such as sodium salt and potassium salt, alkaline earth metal salts such as magnesium salt and calcium salt, aluminum salt and zinc salt.

Examples of the ammonium salts are ammonium salt and tetramethylammonium salt.

Examples of the organic amine addition salts are salts with morpholine and piperidine.

Examples of the amino acid addition salts are salts with glycine, phenylalanine, lysine, aspartic acid and glutamic acid.

The oral preparation for promoting synthesis of tissue collagen, the oral preparation for promoting healing of skin wounds or the oral preparation for preventing or improving skin wrinkles or sagging of the present invention comprises hydroxyproline or a salt thereof, and if necessary, may comprise one or more kinds of pharmaceutically acceptable carriers, and further, active ingredients for other treatments.

The oral preparation for promoting synthesis of tissue collagen, the oral preparation for promoting healing of skin wounds or the oral preparation for preventing or improving skin wrinkles or sagging of the present invention can be produced according to arbitrary methods well known in the technical field of pharmaceutics by mixing hydroxyproline or a salt thereof with carriers according to need.

In preparing the oral preparation for promoting synthesis of tissue collagen, the oral preparation for promoting healing of skin wounds or the oral preparation for preventing or improving skin wrinkles or sagging of the present invention, additives such as excipients, binders, disintegrating agents, lubricants, dispersants, suspending agents, emulsifiers, diluents, buffers, antioxidants and bacterial inhibitors can be used.

The agent of the present invention can be in preparation forms such as tablets, powders, granules, emulsions, syrups and capsules.

When the preparation form is a liquid preparation such as syrup, the preparation can be prepared by adding water, sugars (e.g., sucrose, sorbitol and fructose), glycols (e.g., polyethylene glycol and propylene glycol), oils (e.g., sesame oil, olive oil and soybean oil), antiseptics (e.g., p-hydroxybenzoates), flavors (e.g., strawberry flavor and peppermint), and the like.

In the case of tablets, powders, granules, etc. suitable for oral administration, they can be prepared by adding excipients such as sugars (e.g., lactose, white sugar, glucose, sucrose, mannitol and sorbitol), starch (e.g., potato starch, wheat starch and corn starch), inorganic substances (e.g., calcium carbonate, calcium sulfate, sodium hydrogencarbonate and sodium chloride) and plant powders (e.g., licorice powder and gentian powder), disintegrating agents such as starch, agar, gelatin powder, crystalline cellulose, carmellose sodium, carmellose calcium, calcium carbonate, sodium hydrogencarbonate and sodium alginate, lubricants such as magnesium stearate, talc, hydrogenated vegetable oil, macrogol and silicone oil, binders such as polyvinyl alcohol, hydroxypropyl cellulose, methyl cellulose, ethyl cellulose, carmellose, gelatin and starch paste, surfactants such as fatty acid esters, plasticizers such as glycerin, and the like.

The preparations suitable for oral administration may also comprise additives generally used in foods and drinks such as sweeteners, coloring agents, preservatives, thickening stabilizers, antioxidants, color developers, bleaching agents, fungicides, gum bases, bitter agents, enzymes, glazing agents, sour agents, seasonings, emulsifiers, nutrient supplements, manufacture facilitating agents, flavors and spice extracts.

The preparations suitable for oral administration may be used as such, or in any of the forms such as powder foods, sheet-shaped foods, bottled foods, canned foods, retort pouched foods, capsule foods, tablet foods, liquid foods and health drinks, and may also be used as foods and drinks such as health foods, functional foods, food supplements and foods for specified health uses for promoting synthesis of tissue collagen, promoting healing of skin wounds, or preventing or improving skin wrinkles or sagging.

The concentration of hydroxyproline or a salt thereof in the oral preparation of the present invention is appropriately selected depending upon the kind of the oral preparation, the effect expected by the administration of the oral preparation, etc., but it is usually 0.1 to 100% by weight, preferably 0.5 to 70% by weight, particularly preferably 1 to 50% by weight in terms of hydroxyproline or a salt thereof.

The dose of the oral preparation of the present invention varies depending upon the administration route, the age and body weight of a subject of administration, etc. Usually, the agent is administered in a dose of 5 to 5000 mg, preferably 50 to 5000 mg, more preferably 500 to 5000 mg per day for an adult in terms of hydroxyproline or a salt thereof at once or in several portions. There is no specific restriction as to the period of administration, but it is usually one day to one year, preferably one week to three months.

The oral preparation of the present invention can be used not only for humans but also for animals other than humans (hereinafter abbreviated as nonhuman animals).

Nonhuman animals include animals other than humans such as mammals, birds, reptiles, amphibians and fish.

In the case of administration to a nonhuman animal, the dose varies depending upon the age and kind of the animal, etc. Usually, the agent is administered once or several times per day in a daily dose of 0.1 to 100 mg, preferably 1 to 100 mg, more preferably 10 to 100 mg per kg of body weight in terms of hydroxyproline or a salt thereof.

There is no specific restriction as to the period of administration, but it is usually one day to one year, preferably one week to three months.

The effect of hydroxyproline on promotion of the synthesis of collagen in the skin, promotion of wound-healing and improvement of skin wrinkles or sagging was examined and the results are shown in the following test examples.

Test Example 1

HOS:HR-1 mouse (seven-week-old female; purchased from Japan SLC, Inc.) was used in the test.

Trans-4-hydroxy-L-proline (Kyowa Hakko Kogyo Co., Ltd.; hereinafter referred to as hydroxyproline) was dissolved in purified water at a concentration of 50 mg/ml, and the resulting solution was orally administered in an amount of 500 mg/kg. After 0.5, 1, 2, 4, 6 and 24 hours, blood was collected from the abdominal vena cava of the mouse under diethyl ether inhalation anesthesia to obtain a serum. After cervical dislocation, dorsal skin was collected, subjected to freeze-disruption and then to extraction with water to obtain a skin extract.

The amount of hydroxyproline in the sera and the skin extract was analyzed by high performance liquid chromatography using ODS column (4.6 cm φ×15 cm, GL Sciences Inc.) after protein was removed with an equal amount of 2% (w/v) sulfosalicylic acid and the second amino group was labeled with NBD-Cl (4-chloro-7-nitro-2,1,3-benzoxadiazole, Tokyo Chemical Industry Co., Ltd.).

Figure 2:
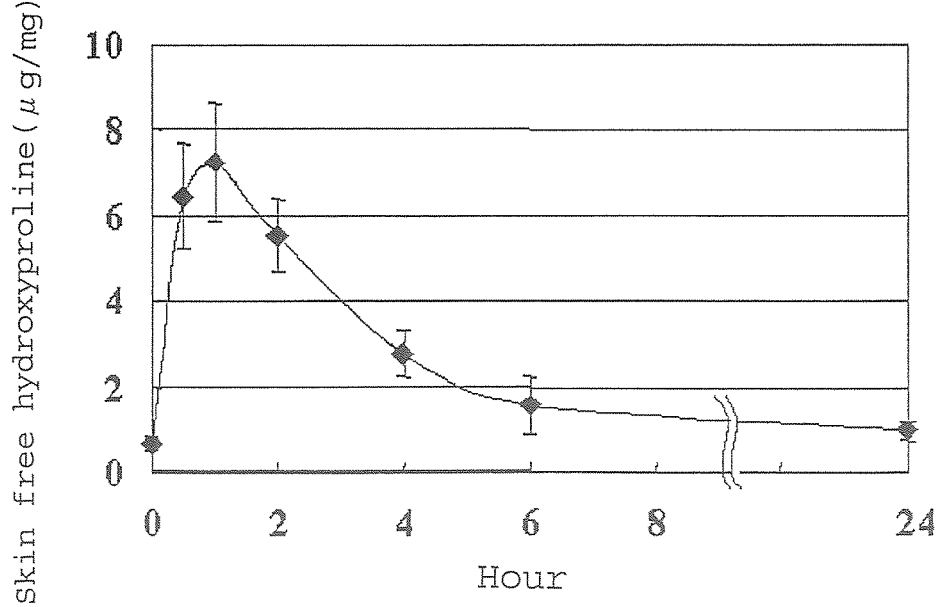
FIG. 2 is a graph showing the concentration of free hydroxyproline in the skin after oral intake of hydroxyproline.

The results are shown in FIGS. 1 and 2. It was revealed that the orally ingested hydroxyproline quickly moves into blood and skin.

Test Example 2

F344/DuCrlCrlj rats (12 heads, 29-week-old male; purchased from Charles River Laboratories Japan, Inc.) were divided into 2 groups each consisting of 6 rats.

The rats of Group 1 and Group 2 were fed with the feed of Example 5 and the control feed of Comparative Example 1, respectively, ad libitum for 7 days. The abdominal area of each rat was shaved with clippers under anesthesia by intraperitoneal administration of pentobarbital, and cut sponge pieces (ca. 150 mg, 2 mm thick, ca. 38 mm×12 mm; Ivalon, Inc.) were inserted into two spots under the skin, followed by suturing. After further feeding for 7 days, the sponge pieces were taken out.

The sponge pieces were subjected to reaction using 6N hydrochloric acid (20 ml/piece) at 110° C. for 18 hours to decompose them with acid and heat. The products obtained by decomposition with acid and heat were diluted 10 times with 1M borate buffer (pH 10.6), and the amount of hydroxyproline was measured in the same manner as in Test Example 1 and was regarded as an index of the collagen-synthesizing ability and tissue-restoring ability of a rat.

The values were shown in terms of average value ±standard deviation and a test of statistical significance was performed by Student's t-test.

TABLE 1

|  | Amount of hydroxyproline/ amount of sponge (μg/g) | Significance by 2 sample t-test |
|---|---|---|
| Group 1 | 4854.1 ± 1340.8 | $p < 0.05$ |
| Group 2 | 2643.6 ± 1105.4 |  |

The results are shown in Table 1. From the fact that the amount of hydroxyproline derived from heat-decomposed collagen was significantly increased in the rats of Group 1 which received hydroxyproline, it was revealed that the synthesis of collagen in the skin was promoted, and as a result, restoration of tissues, that is, wound-healing, was promoted.

Test Example 3

Females aged 47 to 65 years (21 subjects) who chronically suffer from dry skin and rough skin were divided into two groups. After a 2-week observation period, Group 1 (9 subjects) and Group 2 (12 subjects) ingested hard capsules of Example 6 and hard capsules of Comparative Example 2, respectively, for 4 weeks (2 capsules each morning and evening). The test was carried out by parallel-group double-blind test. At the start and the end of the period of ingesting hard capsules, the following questions 1 to 3 were addressed to the subjects (answer "1": level 1, answer "10": level 10) and the skin conditions of the subjects were evaluated by a 10-level rating system.

Question 1: Evaluate the level of wrinkles on your face.
  1: Wrinkles all over the surface
  10: No wrinkles
Question 2: Evaluate the elasticity of the skin of your face.
  1: No elasticity
  10: Extreme elasticity
Question 3: Evaluate the firmness of the skin of your face.
  1: No firmness
  10: Good firmness In the above evaluation, a higher level indicates that a subject feels that the skin wrinkles were more improved in Question 1 and that the elasticity and firmness associated with skin sagging were more enhanced in Questions 2 and 3, respectively. The improvement rate (%) was calculated according to Equation 1.

$$\text{Improvement rate (\%)} = \text{average value of levels after intake} / \text{average value of levels before intake} \times 100 \qquad \text{[Equation 1]}$$

The obtained results are shown in Table 2. The values in the table are the average values.

TABLE 2

| Question | Subject | Before intake (level) | After intake (level) | Improvement rate (%) |
|---|---|---|---|---|
| Question 1 | Group 1 | 5.33 | 6.44 | 120.8 |
| Level of wrinkles | Group 2 | 5.33 | 5.25 | 98.4 |
| Question 2 | Group 1 | 4.67 | 6.89 | 147.6 |
| Skin elasticity | Group 2 | 5.67 | 5.33 | 94.1 |
| Question 3 | Group 1 | 4.56 | 6.44 | 141.5 |
| Skin firmness | Group 2 | 4.08 | 5.17 | 126.5 |

From Table 2, it was revealed that wrinkles and sagging of the face are improved by ingesting trans-4-hydroxy-L-proline.

From the above test examples, it was indicated that orally ingested hydroxyproline moves to the skin and exhibits the effects of promoting synthesis of collagen, healing wounds and improving skin wrinkles or sagging.

Certain embodiments of the present invention are illustrated in the following examples.

Example 1

Preparation of Tablets Comprising Hydroxyproline

Tablets comprising trans-4-hydroxy-L-proline are prepared according to an ordinary method. That is, the following ingredients are uniformly mixed and the resulting mixture is tabletted using a single tablet press to obtain tablets for promoting synthesis of tissue collagen (diameter, 5 mm; weight, 15 mg).

TABLE 3

| Ingredient | Amount (g) |
|---|---|
| Trans-4-hydroxy-L-proline | 10.0 |
| Lactose | 90.0 |
| Dry corn starch | 2.0 |
| Talc | 1.8 |
| Magnesium stearate | 0.2 |

Example 2

Preparation of Granules Comprising Hydroxyproline

The tablets obtained in Example 1 are ground, granulated and sieved to obtain granules for promoting healing of skin wounds (20 to 50 mesh).

Example 3

Preparation of a Drink Comprising Hydroxyproline

A drink for promoting synthesis of tissue collagen comprising trans-4-hydroxy-L-proline is prepared by uniformly dissolving the following ingredients with stirring and adding purified water to make a total volume of 1000 ml. "Appropriate amount" in the following table refers to an amount used for preparing an ordinary drink in respect of flavor and pigment and refers to an amount necessary to make a total volume of 1000 ml by addition of purified water to the remaining ingredients in respect of purified water.

TABLE 4

| Ingredient | Amount (g) |
|---|---|
| Trans-4-hydroxy-L-proline | 5.0 |
| Sodium benzoate | 1.0 |
| Fructose | 10.0 |
| Flavor | appropriate amount |
| Pigment | appropriate amount |
| Purified water | appropriate amount |

Example 4

Preparation of Candies Comprising Hydroxyproline

Candies for promoting healing of skin wounds comprising trans-4-hydroxy-L-proline which are composed of the following ingredients are prepared according to an ordinary method.

TABLE 5

| Ingredient | Amount (g) |
|---|---|
| Trans-4-hydroxy-L-proline | 1.00 |
| Sorbitol powder | 98.75 |
| Flavor | 0.20 |
| Sorbitol seed | 0.05 |

Example 5

Preparation of a Feed for Animals Comprising Hydroxyproline

A feed for animals comprising trans-4-hydroxy-L-proline which is composed of the following ingredients was prepared according to an ordinary method.

TABLE 6

| Ingredient | Amount (g) |
|---|---|
| Trans-4-hydroxy-L-proline | 1.0 |
| Casein | 25.0 |
| Sucrose | 40.2 |
| Cellulose | 5.0 |
| Choline bitartrate | 0.2 |
| DL-Methionine | 0.4 |
| L-Aspartic acid | 6.7 |
| Corn starch | 12.0 |
| Corn oil | 5.0 |
| AIN76 vitamin mix (No Choline added) | 3.5 |
| AIN76 mineral mix | 3.5 |

Example 6

Preparation of Capsules Containing Hydroxyproline

The following ingredients were weighed, put into a mixer and sufficiently mixed to obtain a uniform mixture. The mixture was encapsulated in hard gelatin capsules according to an ordinary method to obtain hard capsules containing trans-4-hydroxy-L-proline (ca. 500 mg/capsule).

TABLE 7

| Ingredient | Amount (mg) |
| --- | --- |
| Trans-4-hydroxy-L-proline | 500.0 |
| Microcrystalline cellulose | 97.5 |
| Colloidal silicon dioxide | 12.5 |
| Magnesium stearate | 12.5 |

Comparative Example 1

A feed for animals was prepared using L-aspartic acid in place of trans-4-hydroxy-L-proline of Example 5.

Comparative Example 2

Hard capsules were prepared using corn starch in place of trans-4-hydroxy-L-proline of Example 6.

INDUSTRIAL APPLICABILITY

The present invention can provide an oral preparation for promoting synthesis of tissue collagen, an oral preparation for promoting healing of skin wounds or an oral preparation for preventing or improving skin wrinkles or sagging, which comprises hydroxyproline or a salt thereof as an active ingredient.

The invention claimed is:

1. A method for promoting synthesis of tissue collagen in skin, which comprises orally administering to a human having skin wrinkles or sagging an effective amount of a composition comprising hydroxyproline or a salt thereof, wherein
   said hydroxyproline or salt thereof being the only active ingredients in said composition,
   said skin wrinkles or sagging are induced by aging, and the tissue collagen synthesized improves said skin wrinkles or sagging.

2. The method according to claim 1, wherein said composition comprises 0.5 to 70% by weight of hydroxyproline or a salt thereof as an active ingredient; and
   a comestible carrier comprising at least one member selected from the group consisting of excipients, binders, disintegrating agents, lubricants, dispersants, suspending agents, emulsifiers, diluents, buffers, antioxidants and bacterial inhibitors, wherein
   said oral preparation is in the form of a tablet, powder, granule, emulsion, syrup or capsule.

3. The method according to claim 1, wherein said composition is a solid.

4. The method according to claim 1, wherein 5 to 5,000 mg of said hydroxyproline or salt thereof is administered to said human per day.

5. The method according to claim 4, wherein said hydroxyproline or salt thereof is administered to said human at 0.1 to 100 mg per kg body weight per day.

6. The method according to claim 5, wherein 50 to 5,000 mg of said hydroxyproline or salt thereof is administered to said human per day.

7. The method according to claim 6, wherein said hydroxyproline or salt thereof is administered to said human at 1 to 100 mg per kg body weight per day.

8. The method according to claim 7, wherein 500 to 5,000 mg of said hydroxyproline or salt thereof is administered to said human per day.

9. The method according to claim 8, wherein said hydroxyproline or salt thereof is administered to said human at 10 to 100 mg per kg body weight per day.

10. The method according to claim 1, wherein said composition comprises said hydroxyproline salt, said salt being selected from the group consisting of hydrochloride, sulfate, nitrate, phosphate, acetate, maleate, fumarate, citrate, malate, lactate, α-ketoglutarate, gluconate, caprylate, sodium, potassium, magnesium, calcium, aluminum, zinc, ammonium, tetramethylammonium, morpholine, piperidine, glycine, phenylalanine, lysine, asparate and glutamate salts.

11. The method according to claim 1, wherein said composition further comprises at least one member selected from the group consisting of sucrose, sorbitol, fructose, polyethylene glycol, propylene glycol, sesame oil, olive oil, soybean oil, p-hydroxybenzoate, strawberry flavor and peppermint.

12. The method according to claim 3, wherein said composition further comprises at least one member selected from the group consisting of lactose, white sugar, glucose, sucrose, mannitol, sorbitol, potato starch, wheat starch, corn starch, calcium carbonate, calcium sulfate, sodium hydrogencarbonate, sodium chloride, licorice powder, gentian powder, agar, gelatin powder, crystalline cellulose, carmellose sodium, carmellose calcium, sodium alginate, magnesium stearate, talc, hydrogenated vegetable oil, macrogol, silicone oil, polyvinyl alcohol, hydroxypropyl cellulose, methyl cellulose, ethyl cellulose, fatty acid esters and glycerin.

* * * * *

UNITED STATES PATENT AND TRADEMARK OFFICE
CERTIFICATE OF CORRECTION

| | |
|---|---|
| PATENT NO. | : 9,433,605 B2 |
| APPLICATION NO. | : 13/856566 |
| DATED | : September 6, 2016 |
| INVENTOR(S) | : Toshikazu Kamiya et al. |

Page 1 of 1

It is certified that error appears in the above-identified patent and that said Letters Patent is hereby corrected as shown below:

On the Title Page

Item (56) REFERENCES CITED:

Foreign Patent Documents, "WO 2000-051561 9/2000" should read --WO 2000/051561 9/2000--.

In the Specification

COLUMN 7:

Line 8, "intakex" should read --intake x--.

Signed and Sealed this
Third Day of January, 2017

Michelle K. Lee
*Director of the United States Patent and Trademark Office*